US00PP20492P3

(12) United States Plant Patent
Woolmore

(10) Patent No.: US PP20,492 P3
(45) Date of Patent: Nov. 17, 2009

(54) ***METROSIDEROS* PLANT NAMED 'TAHITIAN SUNSET'**

(50) Latin Name: *Metrosideros collina*
Varietal Denomination: Tahitian Sunset

(76) Inventor: Malcolm Woolmore, 82 Trig Road, Whenuapai, Auckland (NZ)

( * ) Notice: Subject to any disclaimer, the term of this patent is extended or adjusted under 35 U.S.C. 154(b) by 19 days.

(21) Appl. No.: 11/998,815

(22) Filed: Dec. 1, 2007

(65) Prior Publication Data

US 2008/0313783 P1 Dec. 18, 2008

(51) Int. Cl.
*A01H 5/00* (2006.01)

(52) U.S. Cl. ..... Plt./263.1

(58) Field of Classification Search ..... Plt./263.1
See application file for complete search history.

*Primary Examiner*—Annette H Para
(74) *Attorney, Agent, or Firm*—Mark P. Bourgeois

(57) ABSTRACT

A new cultivar of *Metrosideros* plant named 'Tahitian Sunset' that is characterized by green and yellow variegated leaves, coral colored flowers and short internodes.

1 Drawing Sheet

Botanical classification: *Metrosideros collina.*

Variety denomination: 'Tahitian Sunset'.

BACKGROUND OF THE INVENTION

The present invention relates to a new and distinct cultivar of *Metrosideros* plant botanically known as *Metrosideros collina* and hereinafter referred to by the cultivar name 'Tahitian Sunset'.

The cultivar 'Tahitian Sunset' was discovered as a naturally occurring branch mutation of *Metrosideros collina* 'Tahiti' (not patented). 'Tahitian Sunset' was discovered in 2004 in a cultivated area of Auckland, New Zealand.

Asexual reproduction of the new cultivar 'Tahitian Sunset' first occurred by softwood tip cuttings in 2004 in Auckland, New Zealand. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Metrosideros* cultivar 'Tahitian Sunset'. These traits in combination distinguish 'Tahitian Sunset' as a new and distinct cultivar apart from other existing known varieties of *Metrosideros.*

1. 'Tahitian Sunset' exhibits green and yellow variegated leaves.
2. 'Tahitian Sunset' exhibits coral colored flowers.
3. 'Tahitian Sunset' exhibits short internodes.

The closest comparison cultivar is the parent plant *Metrosideros* 'Tahiti'. 'Tahitian Sunset' is distinguishable from 'Tahiti' by the following characteristics:

1. 'Tahitian Sunset' exhibits green and yellow variegated leaves. The leaves of 'Tahiti' are green.

2. 'Tahitian Sunset' exhibits a shorter internode length than the internode length of 'Tahiti'.

BRIEF DESCRIPTION OF THE DRAWING

The accompanying photographs illustrates the distinguishing traits of *Metrosideros* 'Tahitian Sunset'.

The plant in the photograph of sheet 1 shows an overall view of a 1 year old plant.

The photograph of sheet 2 shows a close-up view of the flowers.

The photographs were taken using conventional techniques and although colors may appear different from actual colors due to light reflectance it is as accurate as possible by conventional photographic techniques.

BOTANICAL DESCRIPTION OF THE PLANT

The following is a detailed description of the new *Metrosideros* cultivar named 'Tahitian Sunset'. Data was collected in Auckland, New Zealand from 1 year old plants grown outdoors in 1.5 liter containers. The time of year was Spring in the Southern Hemisphere and the temperature range was 12–18 degrees Centigrade during the day and 4–11 degrees Centigrade at night. The light level was natural outdoor light. Color determinations are in accordance with The Royal Horticultural Society Colour Chart 2001 edition, except where general color terms of ordinary dictionary significance are used. The growing requirements are similar to the species. 'Tahitian Sunset' has not been tested under all possible conditions and phenotypic differences may be observed with variations in environmental, climatic, and cultural conditions, however, without any variance in genotype.

Botanical classification: *Metrosideros collina* 'Tahitian Sunset'.

Parentage: 'Tahitian Sunset' is a naturally occurring branch mutation of *Metrosideros* 'Tahiti'.

Vigor: Semi vigorous.

Growth habit: Rounded.

Plant shape: Rounded.

Suitable container size: 1.5 L pots.

Height: 100 cm. in height.
Width: 80 cm. in width.
Low temperature tolerance: 4° Centigrade.
High temperature tolerance: 28° Centigrade.
Propagation: Soft wood tip cuttings and tissue culture.
Time to initiate roots in summer: 40 days to initiate roots at 22° Centigrade.
Time to initiate roots in winter: 40 days to initiate roots at 22° Centigrade.
Time to produce a rooted cutting or liner in summer: 90–120 days at 18–24° Centigrade.
Time to produce a rooted cutting or liner in winter: 90–120 days at 10–15° Centigrade.
Growth rate: Approximately 15 cm. per year.
Root system: Fine and fibrous.
Stem:
*Branching habit.*—Moderately branched.
*Pinching.*—Pinched at every third set of leaves.
*Number of lateral branches.*—Average 4 branches.
*Lateral branch length.*—10 cm.
*Lateral branch diameter.*—1.5 mm.
*Internode length.*—1 cm.
*Stem shape.*—Square.
*Stem aspect.*—Upright.
*Stem strength.*—Strong.
*Stem color.*—53A with pubescence 196C.
*Pubescence.*—Present, colored 196C.
Foliage:
*Texture.*—Leathery.
*Leaf arrangement.*—Opposite.
*Compound or single.*—Single.
*Quantity of leaves.*—Average 24.
*Leaf shape.*—Elliptic.
*Leaf apex.*—Acute.
*Leaf base.*—Rounded.
*Leaf length.*—3 cm. in length.
*Leaf width.*—1.8 cm. in width.
*Pubescence.*—Young leaves have no pubescence; in mature leaves pubescence is present on both sides.
*Leaf margin.*—Entire.
*Young leaf color* (*lower surface*).—Variegated; mainly 150C, fine margin 143A.
*Young leaf color* (*upper surface*).—Variegated; mainly 2D, fine margin 137A.
*Mature leaf color* (*lower surface*).—Variegated; mainly 3C, fine margin 137B.
*Mature leaf color* (*upper surface*).—Variegated; mainly 2D, fine margin 137A.
*Vein color* (*under surface*).—53D.
*Vein color* (*upper surface*).—53C.
*Leaf attachment.*—Petiolate.
*Petiole dimensions.*—1.5 mm. in length, and 1 mm. in width.
*Petiole color.*—53C.

Flower:
*Inflorescence dimensions.*—3.5–4 cm in height and 8 cm in width.
*Quantity of flowers per inflorescence.*—30–60 flowers per inflorescence.
*Flowering habit.*—Continuous.
*Flower type.*—Terminal and axillary cyme, tuffs of long stamens.
*Natural flowering season.*—Spring to summer but continues throughout the year.
*Flower bud length.*—4–6 mm. in length.
*Flower bud diameter.*—4–6 mm. in diameter.
*Flower bud shape.*—Rounded.
*Bud color.*—46A.
*Flower aspect.*—Upright.
*Flower shape.*—Rounded tuffs of long stamens.
*Flower dimensions.*—2 cm. in diameter and 1.2 cm. in height.
*Petal appearance.*—Upright.
*Petal texture.*—Slightly leathery.
*Number of petals.*—5.
*Petal arrangement.*—Fused into a funnelform.
*Petal margin.*—Entire.
*Petal apex.*—Rounded.
*Petal length.*—4 mm. in length.
*Petal width.*—2 mm.
*Petal color when opening* (*upper side*).—43A.
*Petal color when opening* (*under side*).—43A.
*Petal color fully opened* (*upper side*).—43A.
*Petal color fully opened* (*under side*).—43A.
*Self-cleaning or persistent.*—Self-cleaning.
*Fragrance.*—None.
Reproduction organs:
*Stamen number.*—Over 24.
*Stamen length.*—1.5–2 cm long.
*Stamen color.*—43B.
*Anther shape.*—Oval.
*Anther size.*—Average 0.2 mm.
*Anther color.*—N200A.
*Amount of pollen.*—Low.
*Pollen color.*—1D.
*Pistil number.*—1.
*Pistil length.*—Average 2.5–3 cm. in length.
*Stigma shape.*—Oval.
*Stigma color.*—43B.
*Style length.*—2.5–3 cm.
*Style color.*—43B.
*Ovary color.*—1B.
Fruit and seed: Seed production has not been observed.
Disease and pest resistance: Plants of the new cultivar have not been observed for disease and pest resistance.

The invention claimed is:

1. A new and distinct variety of *Metrosideros* plant named 'Tahitian Sunset' as described and illustrated.

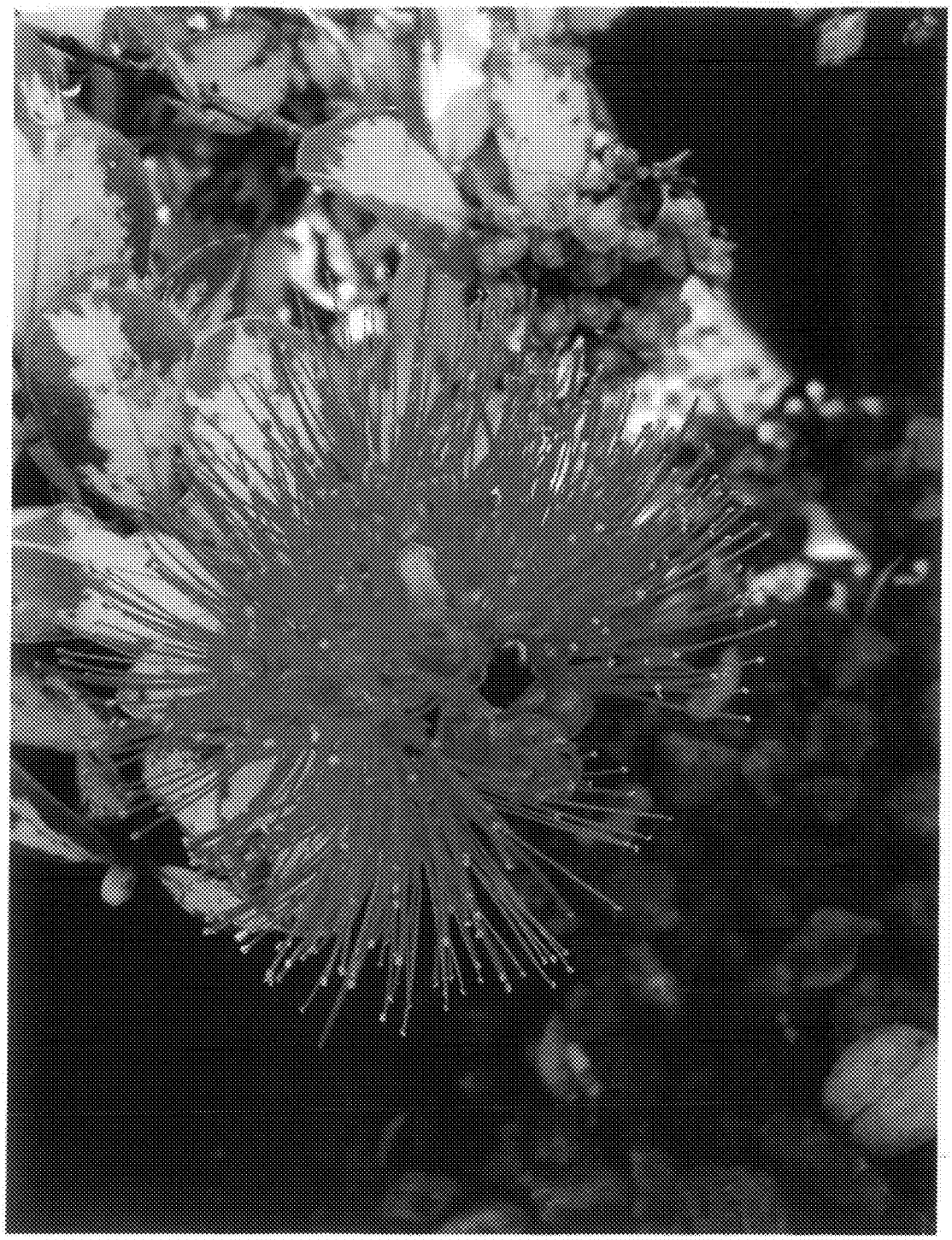

* * * * *